United States Patent
Weijand et al.

[19]

[11] Patent Number: 6,125,300
[45] Date of Patent: Sep. 26, 2000

[54] IMPLANTABLE DEVICE WITH OUTPUT CIRCUITRY FOR SIMULTANEOUS STIMULATION AT MULTIPLE SITES

[75] Inventors: Koen J. Weijand, Rockanje; Robert Leinders, Limbricht, both of Netherlands

[73] Assignee: Medtronic, Inc., Minneapolis, Minn.

[21] Appl. No.: 09/152,072

[22] Filed: Sep. 11, 1998

[51] Int. Cl.[7] ........................................ A61N 1/00
[52] U.S. Cl. ............................................... 607/66
[58] Field of Search .................. 607/66, 4, 5, 9, 607/56, 55, 57

[56] References Cited

U.S. PATENT DOCUMENTS

| | | |
|---|---|---|
| 3,757,791 | 9/1973 | Berkovits . |
| 5,154,172 | 10/1992 | Terry, Jr. et al. . |
| 5,522,865 | 6/1996 | Schulman et al. ............... 607/56 |
| 5,531,774 | 7/1996 | Schulman et al. ............... 607/56 |

OTHER PUBLICATIONS

Programmable High–Amplitude Balanced Stimulus Current–Source for Implantable Microstimulators–S. Bourret et al. (Proceedings –19th International Conference–IEEE/EMBS Oct. 30, –Nov. 2, 1997).
08/915,677 Aug. 21, 1997, Weijand.

*Primary Examiner*—Scott M. Getzow
*Attorney, Agent, or Firm*—Thomas F. Woods; Harold Patton; Michael J. Jaro

[57] ABSTRACT

There is provided an implantable device with two or more output stages for delivering concurrent output pulses to two or more sites within a patient's body. Each output circuit has a common architecture, including a switchable generator which has a plurality of storage capacitors and switches for arranging the capacitors either to be charged by the battery, or to discharge a stimulus pulse. A programmable regulator is provided for further regulation of the output voltage; and a multiplexer connects the output to the desired electrodes placed at the patient site. For concurrent dual pulse-dual site stimulation, a pair of active rectifier switches are connected between the negative terminal of each output stage and the battery positive terminal, whereby at the time of concurrent pulse delivery, the output stage having the greatest negative voltage relative to battery plus has its negative terminal connected to the battery plus terminal, while the other output stage is disconnected from the battery so that it floats. This arrangement reduces crosstalk current while ensuring continued positive biasing of the semi-conductor switches in each output stage.

17 Claims, 6 Drawing Sheets

IMPLANTABLE DEVICE WITH OUTPUT CIRCUITRY FOR SIMULTANEOUS STIMULATION AT MULTIPLE SITES

FIELD OF THE INVENTION

This invention relates to implantable stimulator devices with controllable output stages for delivering stimulus pulses and, in particular, a device with output stages for enabling stimulation at two or more different sites within a patient's body at the same time.

BACKGROUND OF THE INVENTION

In the field of implantable stimulator devices, there are now frequent applications where two or more stimulus pulses are delivered substantially simultaneously, or concurrently, at different sites within a patient's body. Thus, in the fields of neurostimulation and cardiac pacing, for example, the implanted system may be required to generate and deliver such concurrent pulses to two or more positions. As used herein, the terms "concurrent" and "simultaneous" are used to mean either at exactly the same time or substantially the same time, e.g., with some overlap.

A problem that arises in such devices is that of crosscurrents from one stimulus channel to another. If, for example, two generators deliver pulses simultaneously, and both generators are referenced to the battery of the implantable device, there may be crosstalk in the form of current flow between the separate sites, as well as current flow through the intended body loads. Such crosstalk can have a very detrimental effect on the stimulus pulse, thereby impairing the ability to properly stimulate. Another detrimental effect is that of increased current flow, and resulting battery drain, which is a serious problem for implanted systems.

A first simple solution to the problem is to have two or more entirely separate generators, powered by separate batteries. This is, of course, very impractical and is not available as a solution for that reason. Another longtime solution has been to use transformer isolation, but that likewise is unacceptable due to the size and expense of one or more transformers. The proposed solution of simply letting each generator float from any reference to the battery at the time of delivering the voltage pulses likewise is not a feasible solution, because of the nature of solid state circuits in use in the output stages. The generators and regulators of a chip such as would be used in a modern implantable device are comprised of FETs or other equivalent semiconductor switch elements which, as is known, must be maintained with the proper bias thereacross. Each FET in an integrated circuit (IC) is biased with respect to system ground, which is tied to the negative terminal of the battery in the illustrative embodiment of this invention. Each FET component has an inherent diode, which is normally back biased when the FET is properly forward biased, such that the diode is not a factor. However, if the required bias, e.g., positive bias, is not maintained across the FET, the diode becomes forward biased, and transforms the FET effectively into a conducting diode. If this situation prevails, the FETs are parasitic transistors, resulting in parasitic crosscurrents. Consequently, any floating arrangement of the output stages must take into account the need to control the state of all voltages developed during stimulation, so as to prevent such inadvertent forward conduction of the diode junctions. There is thus an important need in the field of implantable devices which are battery powered, for enabling controllable generation and delivery of two or more concurrent stimulus pulses to different sites in the patient's body, while avoiding crosstalk current flow and maintaining proper biasing of the FET or other IC elements.

SUMMARY OF THE INVENTION

In view of the above object, there is provided an implantable battery-powered device having two or more output stages which enable stimulation at two or more stimulation sites concurrently, the two or more output stages being supplied from a single battery and without crosscurrents from one stage to another. The stimulator output stages use energy storage devices such as capacitors as temporary floating power sources during stimulation. Two or more such sources with the appropriate stored pacing energy are connected to respective loads for concurrent stimulation. At the time of delivery of the pulses, the load voltages are monitored, and for the IC type described as the preferred embodiment of this invention the load output which is most negative is connected to the positive terminal of the battery, while the other output circuit is disconnected from the battery so that it is floating. Depending on the IC type or process which is utilized, i.e., N or P doped channels, it may be required to reference the load to the battery terminals differently. This connection at time of stimulation achieves the dual aims of eliminating a closed path through a common battery reference, thereby minimizing crosstalk currents; and maintains only positive voltages on the circuit switching elements with respect to system ground, such that no such elements (FETs) are driven to a state of parasitic conduction.

DESCRIPTION OF THE PREFERRED EMBODIMENTS

Figure 1A:
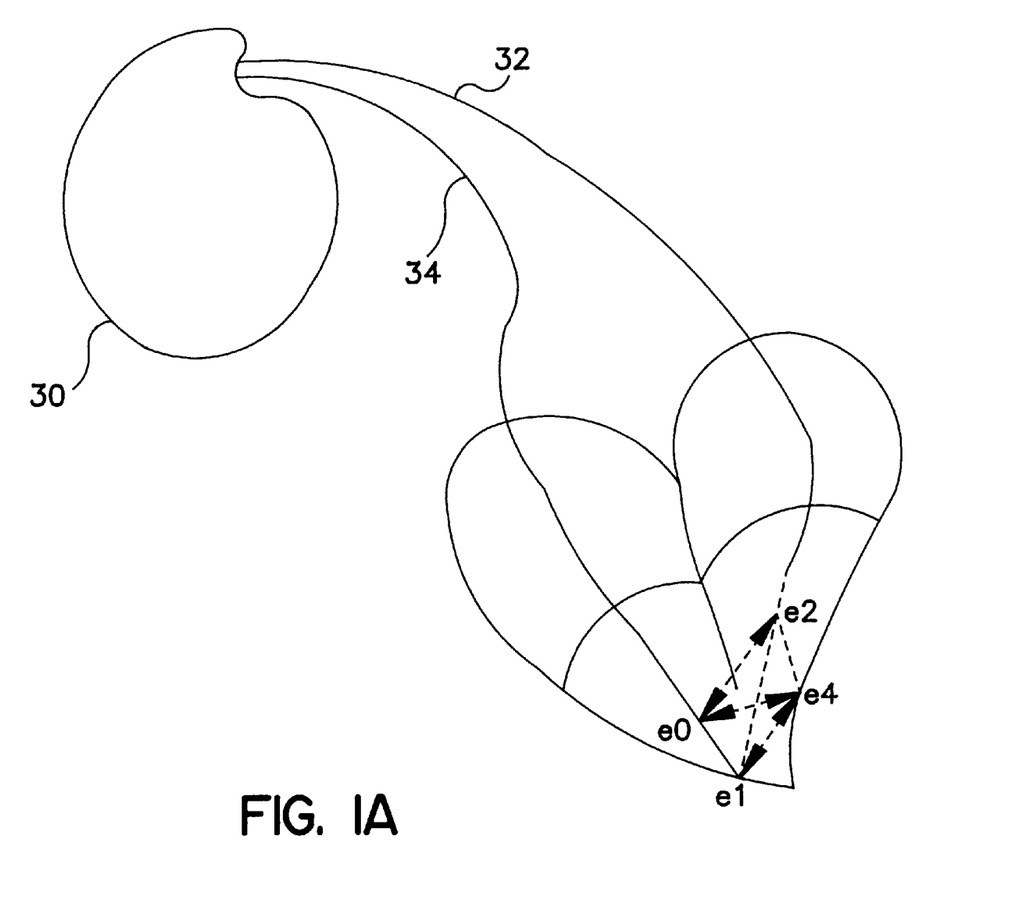
FIG. 1A is a diagrammatic system drawing showing an implanted stimulator device and two leads positioned for concurrent stimulation at two different places in the patient's body.

Referring now to FIG. 1A, there is shown a diagram of an implantable device 30, with leads 32 and 34 for transmitting stimulus pulses to two different sites, or locations in the patient's body, here represented as being within the patient's heart. Each lead has two conductors which carry stimulus pulses to a pair of electrodes, illustrated as e1, e2 and e3,e4. As indicated, for simultaneous delivery of stimulus pulses to the two locations, and without any preventive arrangement, crosstalk currents could flow along the paths indicated by dashed lines. This is illustrated further in connection with FIGS. 4A–4C discussed below.

Figure 1B:
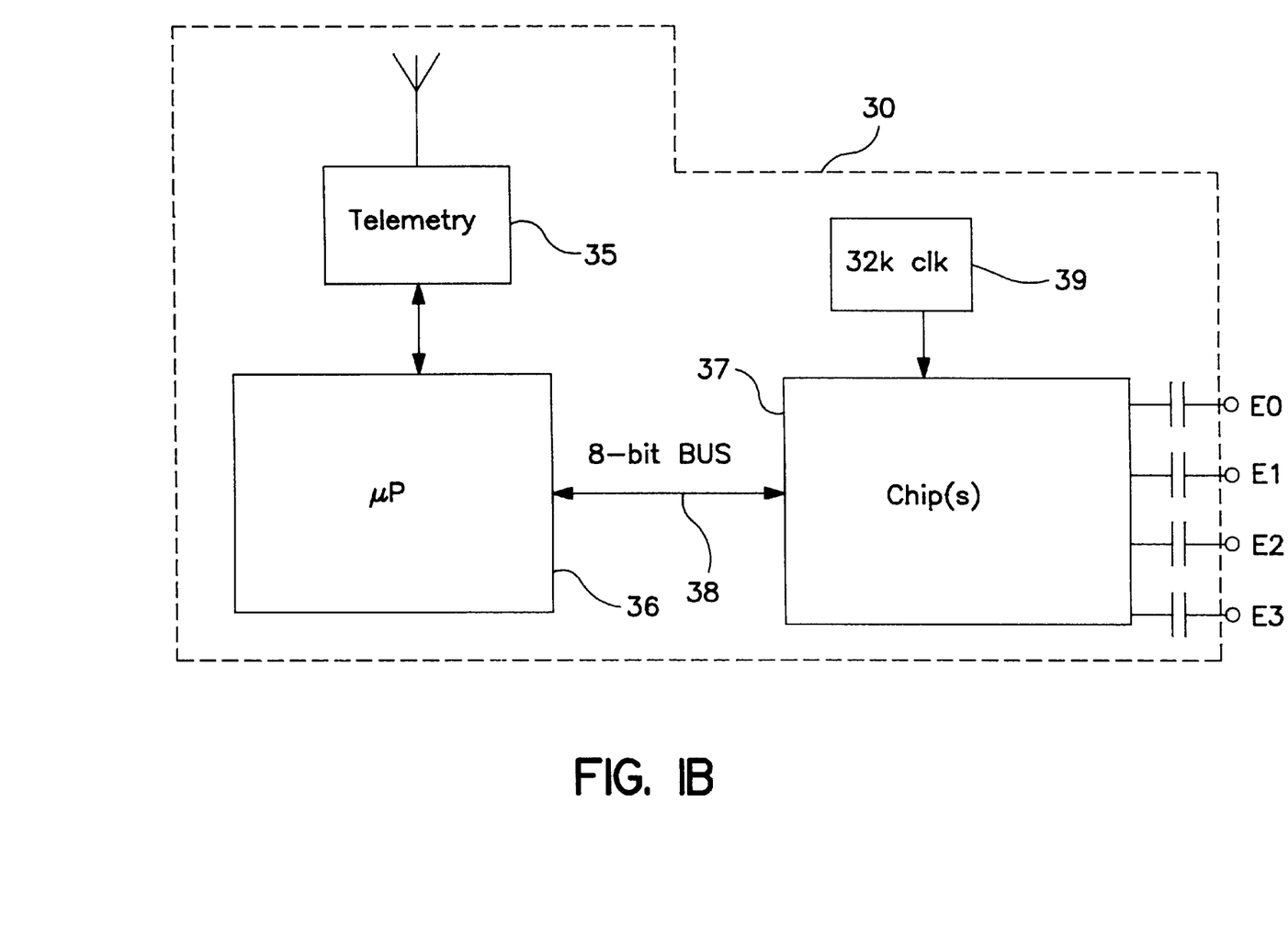
FIG. 1B is a block diagram showing the main system components of an implantable device which provides for two stimulation channels and delivery of stimulus pulses to two different sites.

Referring to FIG. 1B, there is shown a block diagram of a system which includes device 30, for generating stimulus pulses. A telemetry receiver indicated at 35 receives data, e.g., parameter data for control of the stimulus pulses. This data is transmitted to and stored in microprocessor 36, or dedicated logic, which in turn is connected to one or more chips indicated at 37 through a bus 38. The chips contain the generator circuitry for producing output pulses, as set forth in more detail in connection with FIG. 2. A 32 KHz clock, illustrated at 39, operates the registers which control operation of the switches that are contained in chip block 37. It is to be understood that a neurostimulator or pacemaker has other circuit portions which are not illustrated here, for carrying out other control and diagnostic functions, as is well known in the art.

Figure 2:
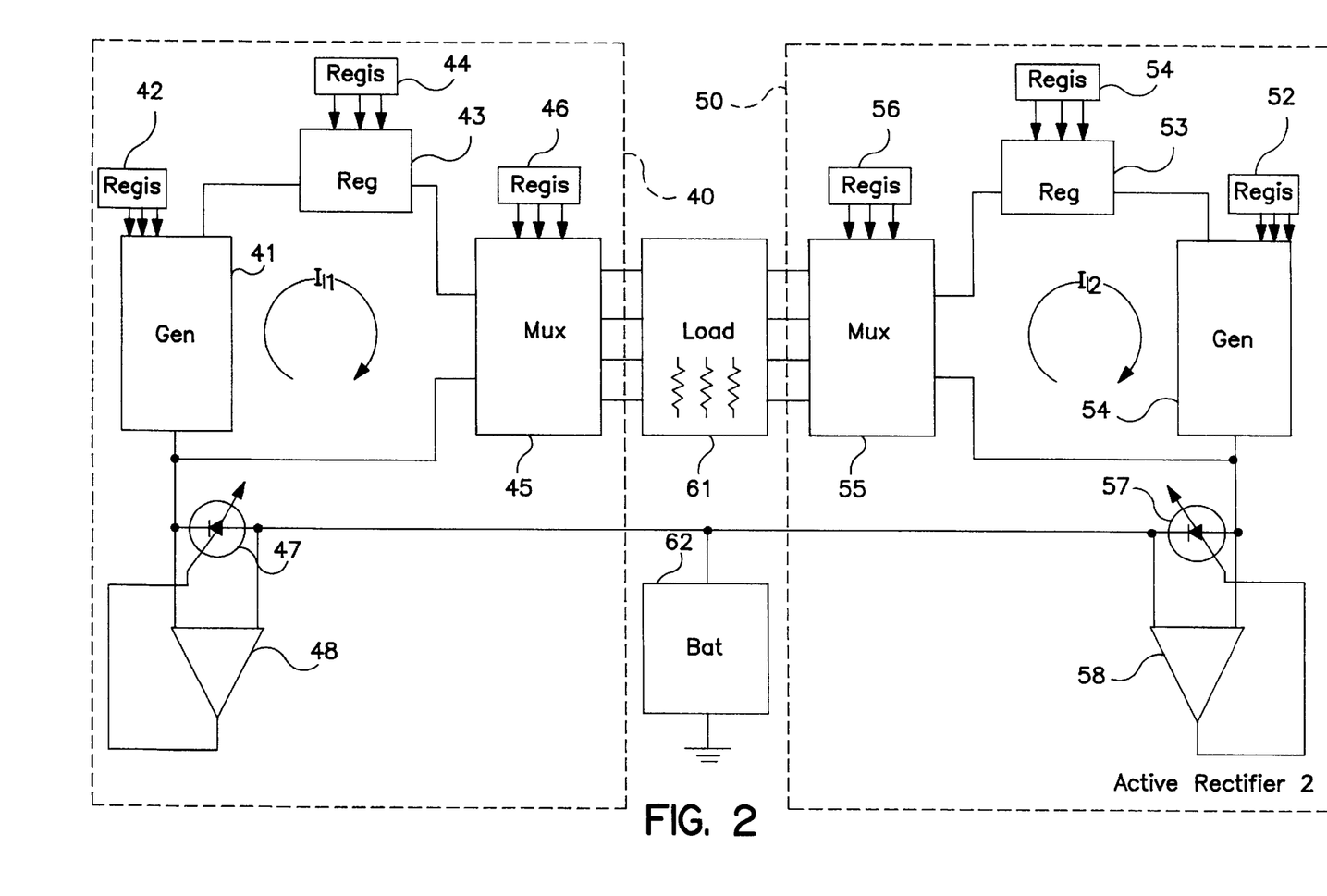
FIG. 2 is a system block diagram showing two output stages, or generator circuits, with connections to patient loads and to the device battery, and also showing circuitry active during delivery of concurrent stimulus pulses for tying a selected one of the out stages to the battery positive terminal and for disconnecting the other output stage so that it is floating.

Referring now to FIG. 2, there is shown a circuit diagram illustrating two output stages, or generator circuits, illustrated as being constructed on two different chips at 40 and 50 respectively. It is to be noted that two or more output stages could be provided on one chip; the ratio of output stages per chip is a function of the real estate required to provide the stimulus energy storage per desired output stage. The invention is not limited in terms of the number of output stages used in a device, or the number of output stages per chip.

Generator blocks 41 and 51 comprise energy storage devices such as capacitors which are used as the power sources during delivery of a stimulus pulse. Generator 41 comprises a plurality of capacitors for storing energy, as well as a switching network for alternately switching the capacitors to receive energy from the battery, and then switching them into a desired configuration for transferring the energy to the load at the time of pulse delivery. The configurations for storing and delivery are controlled through register 42, which in turn is connected to microprocessor 36. Thus, the microprocessor provides timing signals for timing the concurrent pulses, as well as data for control of the pulse parameters, e.g., pulse width, voltage, etc. Generator 41 is in series with a regulator 43, controlled by register 44, in order to adjust or fine tune the voltage output. The voltage output from generator 41 and regulator 43 is transferred to a body site illustrated as part of dual site load 61, through multiplexer 45, which in turn is controlled by register 46. Multiplexer 45 provides the desired connection between the output stage and the load, e.g., it connects to a given lead, and switches output terminals to change polarity. Chip 2 is preferably an identically structured stage, containing generator 51 controlled by register 52; regulator 53 controlled by register 54, and multiplexer 55 controlled by register 56.

It is to be understood that the chip circuit components, i.e., the components of the generators, regulators and multiplexers, are all biased from the device battery by biasing connections not shown. Each generator, regulator and multiplexer comprises a number of switching devices, suitably FETs, which must be maintained with a proper positive biasing, as discussed above.

Still referring to FIG. 2, a battery 62 is shown in circuit connection with each output stage. Active rectifier 47 and differential amplifier 48 are connected between the battery positive terminal and the common negative terminal of generator 41 and the load that it is driving through the multiplexer 45. Likewise, the positive terminal of battery 62 is connected through active rectifier 57 and differential amplifier 58, to the negative terminal of generator 51 and the load it is connected to through multiplexer 55. At the time that the generators 41, 51 are switched into a generator mode, one or the other of rectifier devices 47, 57 will be forward biased, and the other one will be back biased. The differential amplifiers 48, 58 provide a feedback loop to control the switching element, thereby providing instant switching of states. In general, due to circuit connections through the patient's body, one of the loads will have a larger negative voltage across it than the other, such that one of the rectifiers 47, 57 will be switched on and the other switched off. In FIG. 2, if the load driven by generator 41 through multiplexer 45 has the greater negative voltage across it, rectifier 47 will be driven to conduct, and rectifier 57 will be switched off. Under these circumstances, the negative terminal of generator 41 will be raised by the value $+V_B$ such that all FETs on chip 1 will be held positively biased. Chip 2 will be disconnected from battery 62 and thus floating; the voltages on chip 1, or the first output stage 40, will hold all of the biases on output stage 50 in a positive state.

Figure 3A:
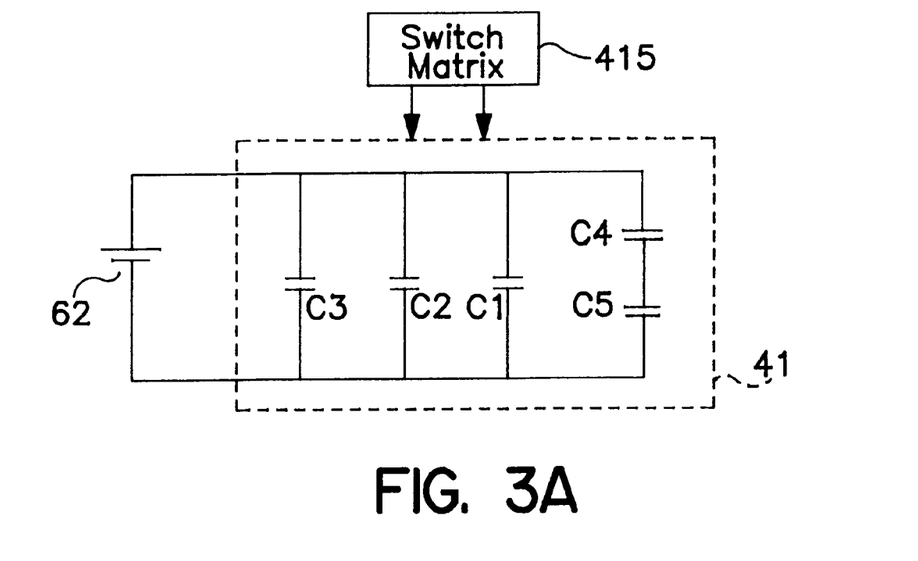
FIG. 3A is a circuit diagram showing the arrangement of a generator circuit in accordance with this invention during the charge state.
Figure 3B:
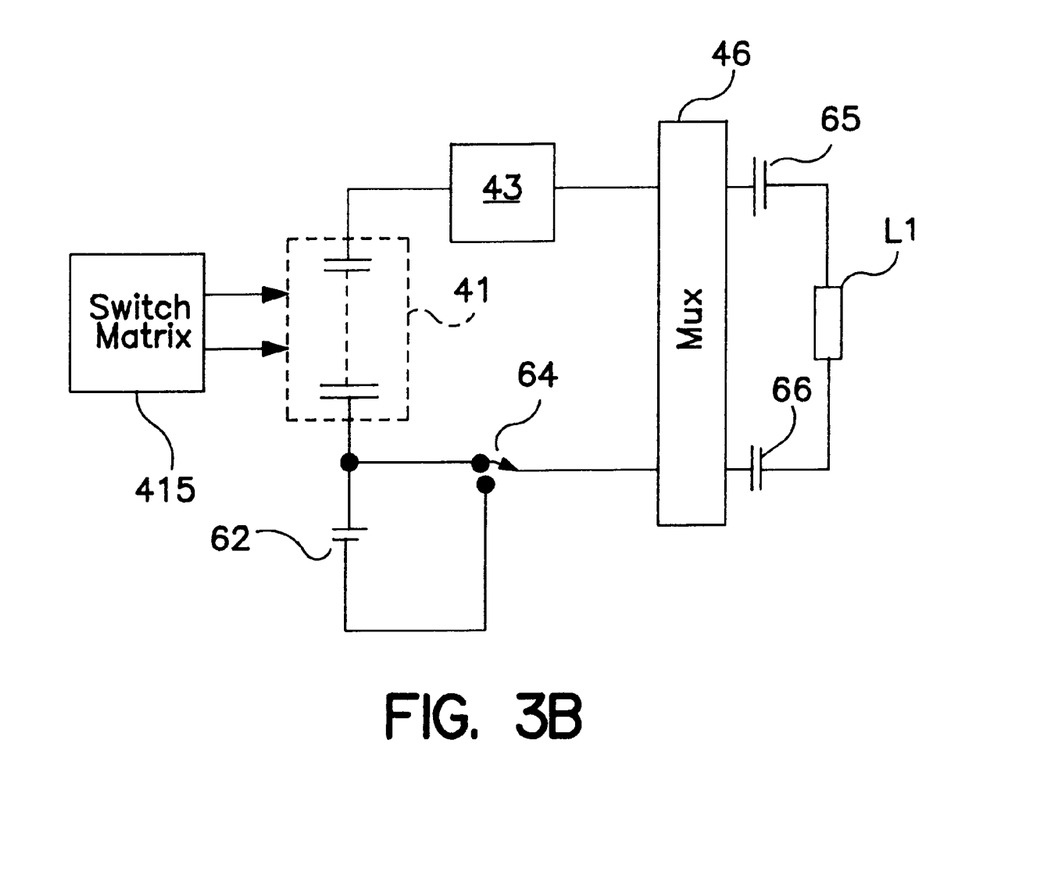
FIG. 3B is a circuit diagram showing the arrangement of a generator circuit in accordance with this invention during the pulse delivery state.

Referring now to FIGS. 3A and 3B, there are shown two circuit diagrams which illustrate the basic principles of the output stage. Each generator circuit includes a network of capacitors and switching elements, in a known fashion. The switching elements can be controlled to tie the capacitors into a charging configuration or into a discharging-pulse delivery configuration. In FIG. 3A, the switches of generator 41, for example, are set by switch matrix 41S to connect a plurality of storage capacitors directly across battery 62. As shown, capacitors C1, C2 and C3 are connected directly across the battery, so that they each are charged fully to battery voltage; capacitors C4 and C5 are connected in series across the battery voltage, such that each is charged to half the battery voltage. In this configuration, the capacitors can provide an output stimulus pulse having n times 0.5 $V_b$. One or more additional capacitors can be used, for example to provide up to five times battery voltage. Whatever the output, it is desirable to charge as many of the capacitors as possible to the full battery voltage, and to utilize the highest capacitor combination, in order to obtain maximum efficiency of charging and discharging the capacitors.

Referring to FIG. 3B, there is shown a circuit diagram illustrating the generator 41 with a predetermined number of capacitors switched into series by switch matrix 41S, to provide a desired output voltage in steps of five-tenths of battery voltage. Regulator 43 provides further bleeding of the voltage, i.e., adjustment to incremental values less than 0.5 $V_B$, in a known manner. If floating stimulation is not required, the battery 62 can be added in series through switch 64, to provide an even higher output voltage. The output voltage is connected through matrix 46 and coupling capacitors 65, 66, to a load illustrated as L1. Generator 51 can be switched in the same manner, to provide a desired multiple of battery voltage. At the same time that generator 41 is switched into such an output stage, generator 51 (FIG. 2) is likewise switched, providing the second, concurrent output voltage which is delivered across a second load. The pulse parameters are determined by the parameter values inputted through the respective registers that control the generators and the regulators. The regulators are, suitably, active only during delivery of a pulse; the output switching matrix is active during delivery of a pulse and after.

Figure 4A:
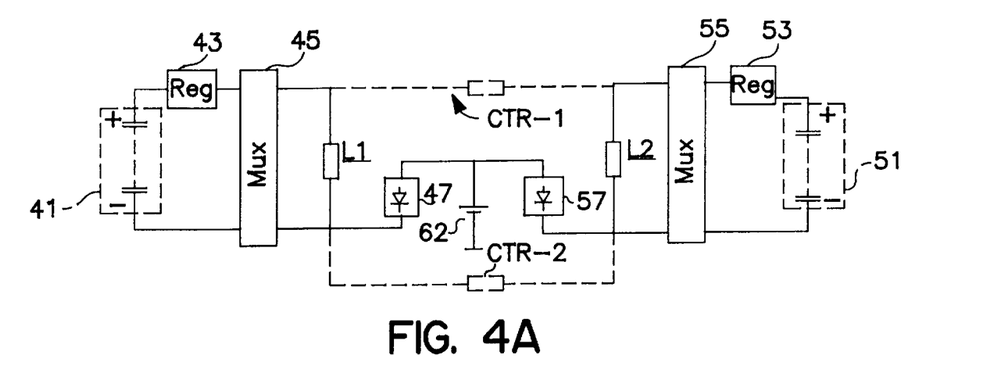
FIG. 4A is a circuit diagram illustrating two generator circuits connected to respective loads, and also illustrating potential crosstalk current paths during concurrent stimulation.

Referring now to FIG. 4A, there is shown a simplified circuit diagram showing connection of two output stages to two respective loads, designated as L1 and L2. Switching elements, or rectifiers 47 and 57, are shown connected between the battery positive terminal and the negative terminal of each load. A resistance designated as CTR-1 is shown in dashed lines connected between the positive side of each load, while a resistance designated as CTR-2 is shown in dashed lines connected between the negative sides of each load. These resistances represent crosstalk resistances through the patient's body, which are indicated by the paths shown in FIG. 1A. Depending upon the sites chosen for delivery of the respective stimulus pulses, usually one of these resistance values will be relatively high and the other relatively low. To avoid crosstalk, it is important that the loads not be tied directly to a common battery terminal, in which event there could be a low resistance loop through just one of the crosstalk paths. For example, if each load negative was tied to battery ground, there would be a loop involving only L1, L2 and CTR-1. If CTR-1 is a relatively low value, then significant crosstalk current would result. However, if the two loads are not connected to a common battery terminal, then both CTR-1 and CTR-2 are in the crosstalk loop, one of which is the relatively higher resistance, such that the crosstalk current is restrained to a minimum value.

Figure 4B:
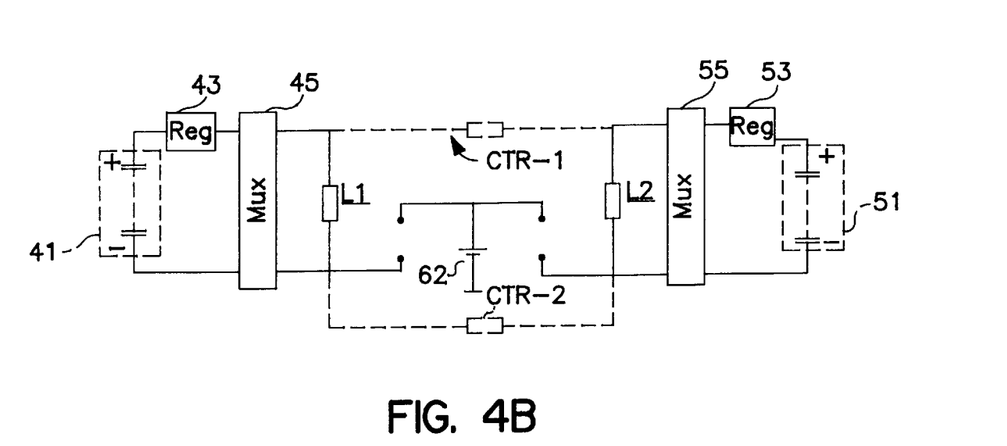
FIG. 4B is the same circuit diagram as FIG. 4A, but modified so that both generators are floating, and illustrating the effect of this situation.
Figure 4C:
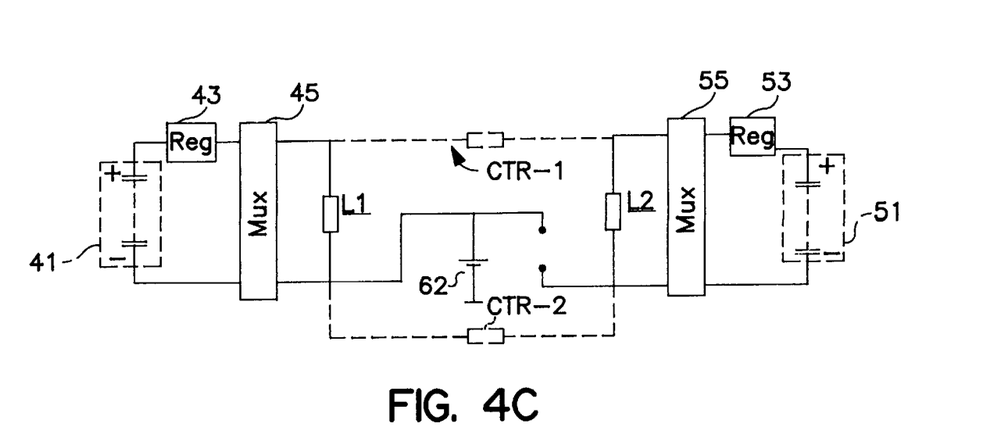
FIG. 4C is the same circuit diagram as FIG. 4A, modified so that the generator with greatest voltage across its load has its negative output terminal connected to the battery plus terminal, while the other generator is floating with respect to the battery.

Referring to FIG. 4B, the same circuit as FIG. 4A is shown, modified by having each output stage floating. In this case, and assuming a voltage of 7 v across L1 and a voltage of 5 v across L2, generator 41 and/or regulator 43 and switch matrix 45 can have FET elements with negative biasing at the time of pulse delivery, resulting in unwanted parasitic currents. Referring to FIG. 4C, the same circuit is shown modified so that during pulse delivery the negative terminal L1 is connected to the positive terminal of the battery, and the second output stage is floating due to the back biasing of switch element 57. In this circumstance, the voltage at the negative terminal of load 1 is tied to $+V_B$, and all voltages on the switches (FETs) of the first output stage are at or higher than $V_B$. The voltages of the second output stage, which is tied to the first generator circuit through the body crosstalk resistances, adjust so that all FET biases in the second output stage are also positive.

Figure 5:
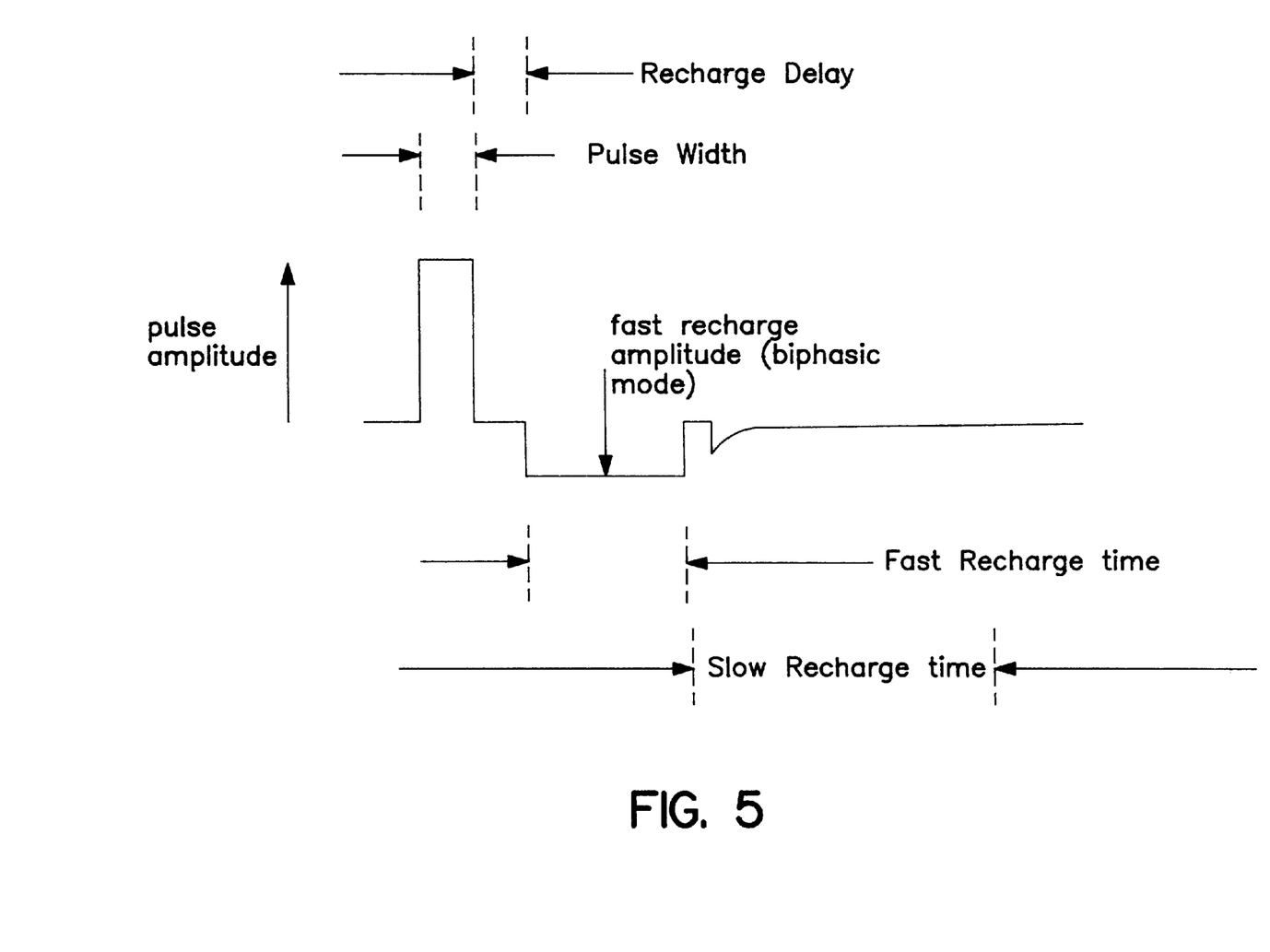
FIG. 5 is a diagram illustrating the programmable parameters of a stimulus which can be delivered with an output stage in accordance with this invention.

The output stages used in the system of this invention can be controlled to provide different types of composite pulses, and to provide bipolar or tripolar stimulation. Tripolar stimulation involves delivering pulses between two respective anodes and one common cathode, for "steering" as is used, e.g., in neuro-stimulation applications. As an example of the programmability of a pulse, reference is made to FIG. 5, showing a biphasic pulse with a positive-going stimulus pulse portion, followed by a fast recharge pulse portion, and a later slow recharge time. Such parameters can be programmed through the microprocessor and the registers that control the generator and the multiplexer. Also, output stages can be stacked by appropriate switching of connections therebetween, to place two or more outputs in series. Thus, the invention is not limited in terms of the number of output stages or the manner in which they are switched into stacking relationship, in order to provide additional flexibility in determining the parameters of the output pulse.

We claim:

1. An implantable stimulator system, said system having a device for generating stimulus pulses and leads for delivering stimulus pulses to at least two patient sites, said device having at least two generator circuits for generating concurrent stimulus pulses and a battery for powering said circuits, each of said circuits comprising IC components, said battery having positive and negative output terminals, and switching means operative during concurrent delivery of pulses by said generator circuits for connecting a predetermined one of said battery terminals to a selected one of said generator circuits and disconnecting the other of said generator circuits from said predetermined battery terminal so that said other generator circuit is floating with respect to said battery, whereby all said IC components are held at a selected bias during said concurrent delivery of pulses and there is no direct circuit connection between said generator circuits.

2. The system as described in claim 1, wherein each of said generator circuits comprises a plurality of capacitors for receiving energy from said battery and for storing said energy until said circuits generate said stimulus pulses.

3. The system as described in claim 1, wherein each of said generator circuits comprises level means for configuring said capacitors to provide a predetermined voltage level, and first register means for programming said predetermined voltage level.

4. The system as described in claim 3, wherein each said generator circuit has a positive output terminal and a negative output terminal, and wherein said switching means comprises a first switching element connected between the negative output terminal of a first of said generator circuits and a predetermined terminal of said battery, and a second switching element connected between the negative output terminal of a second of said generator circuits and said predetermined battery terminal, said switching elements being arranged so that when one is conducting the other is not conducting.

5. The system as described in claim 4, wherein the negative terminal of said battery is system ground for said generator circuits, and wherein each of said switching elements is connected to the battery positive terminal.

6. The system as described in claim 5, wherein said switching elements are arranged so that the generator circuit having the greatest voltage across its output terminals during pulse delivery is connected to said battery positive terminal.

7. The system as described in claim 1, wherein said device is a cardiac pacemaker and said two sites are at different locations in a patient's heart, and comprising pulse control means for controlling the parameters of generated pulses and the concurrent generation of said pulses.

8. The system as described in claim 7, wherein each of said generator circuits has a pair of output terminals, and comprising a first lead connected to the output terminals of a first of said generator circuits for delivering pacing pulses to a first site and a second lead connected to the output terminals of the second generator circuit for delivering pacing pulses to the second site.

9. The system as described in claim 7, comprising a pair of leads for connecting pacing pulses from said generator circuits to different sites, and multiplexer means for providing a plurality of connections of the outputs of said generator circuits to said leads.

10. An implantable device for delivering concurrent pulses to a pair of sites in a human body, comprising first and second matched generator circuits, each of said circuits having a plurality of capacitors and a switching network for switchably connecting said capacitors in respective charging and pulse generating configurations, control means for concurrently switching said capacitors into pulse generating configurations, a battery for powering said networks, said battery having positive and negative output terminals, said networks having semiconductor elements which are normally biased positive with respect to the negative terminal of said battery, and switching means operative when said generator circuits are in pulse generating configurations for connecting one of said generator circuits only to said battery positive terminal and for disconnecting the other of said generator circuits from said battery.

11. The device as described in claim 10, wherein each of said generator circuits has a positive output terminal and a negative output terminal, and said switching means comprises an active switch element connected between each said negative output terminal and the positive battery terminal during generation of said concurrent pulses.

12. The device as described in claim 11, comprising more than two of said generator circuits, each with an output, and multiplexing means connected to the outputs of said generator circuits for providing programmable connections from said outputs to predetermined respective electrical loads.

13. The device as described in claim 12, wherein each of said generator circuits comprises a programmable regulator circuit for control of the circuit output voltage.

14. The device as described in claim 13, comprising programmable control means for controlling the parameters of each of said concurrent pulses.

15. The device as described in claim 10, comprising timing means for timing the generation of said concurrent pulses and the switching of said switching network to configure said generator circuits to respective charging and pulse generating configurations.

16. An implantable stimulator system for concurrently generating and delivering stimulus pulses to at least two sites in a patient, the system having lead means for delivering concurrent pulses to said two sites, and a device for generating said concurrent pulses, said device comprising:

first and second generator circuits, each having positive and negative output terminals, said output terminals of each generator circuit being connected to said lead means so as to provide stimulus pulses to a respective one of said sites;

timing means for controlling said first and second generator circuits to generate pulses concurrently;

a battery for powering said first and second generator circuits, having positive and negative battery terminals; and comparing means operative during delivery of said concurrent pulses for comparing the voltage at a predetermined one of said first generator circuit output terminals with the voltage at a predetermined one said second generator circuit output terminals, and switching means operative as a function of said comparing and during said concurrent pulse delivery for connecting one of said predetermined output circuit terminals to a predetermined one of said battery terminals and for disconnecting the other said predetermined output circuit terminals from said predetermined one battery terminal.

17. The system as described in claim 16, wherein said switching means comprises means for connecting the output circuit terminal with the greatest negative voltage to the positive battery terminal.

* * * * *